(12) United States Patent
Veit (10) Patent No.: US 7,950,098 B2
(45) Date of Patent: May 31, 2011

(54) SUPPORT UNIT FOR A SCRAPER AND METHOD FOR POSITIONING THE SUPPORT ELEMENTS OF A SCRAPER

(75) Inventor: Peter Veit, Zweibrücken (DE)

(73) Assignee: PII Pipetronix GmbH, Stutensee (DE)

( * ) Notice: Subject to any disclaimer, the term of this patent is extended or adjusted under 35 U.S.C. 154(b) by 1054 days.

(21) Appl. No.: 11/604,340

(22) Filed: Nov. 27, 2006

(65) Prior Publication Data

US 2007/0119006 A1 May 31, 2007

(30) Foreign Application Priority Data

Nov. 30, 2005 (DE) .......................... 10 2005 056 969

(51) Int. Cl.
*F16L 55/26* (2006.01)
*G01M 19/00* (2006.01)

(52) U.S. Cl. .................. 15/104.05; 15/104.16; 73/866.5

(58) Field of Classification Search ............... 15/104.05, 15/104.16; 73/866.5
See application file for complete search history.

(56) References Cited

U.S. PATENT DOCUMENTS

| 4,807,484 | A | 2/1989 | Goedecke |
| 6,196,075 | B1 | 3/2001 | Comello |
| 6,339,993 | B1 | 1/2002 | Comello |
| 6,381,797 | B1 | 5/2002 | Filippovitch |
| 7,354,348 | B2 * | 4/2008 | Kapustin et al. .............. 464/119 |
| 2005/0126316 | A1 | 6/2005 | Richter |

FOREIGN PATENT DOCUMENTS

| DE | 203 06 958 | 7/2003 |
| DE | 203 06 958 | 8/2003 |
| EP | 0 078 072 | 5/1983 |
| EP | 1 046 856 | * 10/2000 |
| WO | WO 2004/088301 | 10/2004 |

* cited by examiner

*Primary Examiner* — Randall Chin (57) ABSTRACT

The present invention provides a device and a method for positioning components (3) of a scraper moved through laid pipelines along the inner pipeline wall, the components (3) being located on radially expandable support elements (2) in such a way that with the same spacing between the components and pipe wall for different pipe diameters there is a uniform coverage of the pipe circumference by the components (3). For this purpose in each case at least two support elements (2) succeeding one another in the pipeline circumferential direction are pivotably interconnected by at least one connecting member (4) articulated thereto, so that the support elements (2) are equidistantly spaced in each expansion position.

23 Claims, 5 Drawing Sheets

SUPPORT UNIT FOR A SCRAPER AND METHOD FOR POSITIONING THE SUPPORT ELEMENTS OF A SCRAPER

CROSS REFERENCE TO RELATED APPLICATIONS

This application claims the benefit of priority under 35 U.S.C. §119 of German Patent Application DE 10 2005 056969.2 filed Nov. 30, 2005, the entire contents of which are incorporated herein by reference.

FIELD OF THE INVENTION

The invention relates to a support unit for a scraper movable through a pipeline having radially expandable support elements for receiving components facing the pipe wall, the support elements being successively arranged in the circumferential direction of the pipeline and a method for positioning components facing the pipe wall of a scraper movable through a pipeline having radially expandable support elements for receiving components facing the pipe wall, the support elements being successively arranged in the circumferential direction of the pipeline.

BACKGROUND OF THE INVENTION

Scrapers are used in pipelines, particularly for water, oil or gas transportation, for discovering faults in the pipeline, for cleaning pipelines and the like. These functions are essentially taken over by components located on the outer circumference on support parts, such as sensors for inspecting the state of the pipeline wall. There is a clearly definable spacing between the components and the inner wall or outer wall in the case of different cross-sectional robot sizes. The components are fixed to radially expandable support elements, which succeed one another in the circumferential direction of the pipeline.

In order to be able to use such scrapers in pipelines with different standard widths, such as 26 and 42 inches, or to be able to inject the scrapers via supply lines into the pipeline, test scrapers with radially expandable support structures located on a central pulling part are known and on the circumference thereof are located sensors. Such support structures with a circumference variable as a function of the internal cross-section of the pipeline have several substantially radially arranged support arms pivotable about axes perpendicular to the longitudinal median axis of the pulling part (DE 197 46 510 A1, DE 197 46 511 A1).

It is also known from DE 197 46 511 A1 for the positioning of sensors in circumferentially displaced manner on in each case two support frames which are movable axially against one another and which in the case of a given pipe circumference can be moved into one another in such a way that the sensors cover the entire pipeline circumference. The sensors are not uniformly distributed, because the spacings between the two support frames vary. This construction is relatively complicated and leads to high production costs, because for each different pipe diameter in each case a different support frame is required. It is also desirable to have a greater measurement resolution in the circumferential direction of the pipeline and for this purpose a larger number of sensors relative to the pipe diameter is necessary.

DE 102 10 746 C1 describes a sensor support body of a scraper, in which the individual segments are joined together in the circumferential direction of the pipeline to form a hollow body with a cylindrical surface, the segments in the axial direction comprising at least two successive skid pairs, which are elastically interconnected by connecting elements in order to bring about a high arc traversability of the scraper. EP 255 619 B1 and DE 203 06 958 U1 disclose a sensor support in the form of a sleeve with rubber-like characteristics, which can adapt to the pipe wall and in particular to pipeline unevennesses. These arrangements lead to higher operational and functional reliability of the scraper, but are only suitable for testing pipelines having a standard width. For different pipe diameters different constructions are necessary, which leads to high manufacturing costs and to a considerable storage expenditure.

The problem of the invention is to provide a device of the aforementioned type which, whilst avoiding the aforementioned disadvantages, can be more particularly used in pipelines having different standard widths and has a high operationally reliability, a higher measurement resolution in the circumferential direction and a simple, inexpensive construction.

SUMMARY OF THE INVENTION

In the case of a device of the aforementioned type, the invention solves this problem in that in each case at least two successive support elements are interconnected pivotably by at least one connecting member articulated thereto that the angular spacing of the support elements is varied through connecting members pivotably articulated thereto and connecting the same under the action of radially inwardly or outwardly acting forces in such a way that on expansion or compression the spacing of two successive support elements is increased or decreased by in each case the same amount.

In a device constructed according to the invention, there is consequently a uniform spacing in the circumferential direction of the pipeline between in two respective successive support elements as a result of a pivoting of the connecting elements in or counter to the scraper movement direction during the expansion of the support elements. This leads to a uniform distribution of the components in the circumferential direction of the pipeline in the case of different pipe diameters.

At least two components are arranged in displaced manner in the circumferential direction of the pipeline in each expansion position on the given support elements. Alternatively in a specific expansion position the components on the support elements are positioned parallel to the scraper movement direction.

In a preferred development the components are successively arranged on the support elements in the support element extension direction, so as to form an angle of less than 90° to the scraper movement direction, the support element is curved in the circumferential direction of the pipeline. On changing the expansion position of the support elements, there is a change to the angle of the support element extension direction and the successively positioned components with respect to the scraper movement direction. Following an expansion of the support elements said angle is larger and following a compression of the support elements said angle is smaller. Thus, in different expansion positions there is an uninterrupted arrangement of components over the entire pipe circumference. During the movement of the scrapers through a given axial position of the pipeline, the entire pipe circumference is uniformly traversed by the components at said axial position. Preferably all the components have the same radial spacing from the pipe wall in each expansion state.

In a preferred development, in each case two successive support elements are pivotably interconnected by two articulated connecting members. In addition, a connecting member is so located on three successive support elements that on pivoting the connecting member about an axis at the central support element the spacing of the respective outer support elements from the central support element is increased or decreased by the same amount. This is brought about in that the connecting member is articulated at its centerpiece in the center of the respective central support element and at its end pieces preferably on a front or rear end of one or the other outer support element in an identical distance to the center.

In a preferred construction the connecting members have a double S-shape. The connecting members can also be constructed as support elements for receiving components facing the pipe wall. They can in particular be sensors for carrying out measurements on the pipeline.

The number of support elements can be chosen freely as a function of the pipe wall sizes or the task involved. The number and spacing of the components located on the support elements can also be varied. In a preferred construction the support elements and/or the connecting members are flexibly designed in order to adapt to the pipe wall shape. Thus, even in the case of ovalizations, bulges or other noncircularities of the pipeline a high operability is ensured. The support elements can be formed by a flexible base element, such as spring steel or plastic, or from several flexibly interconnected components. In an advantageous construction the connecting members have the same resistance moment as the support elements. More particularly if the connecting members act in the manner of springs, a high adaptability of the support unit to the geometrical conditions is ensured.

For radial positioning purposes the support elements can be located on a support frame and supported by the latter. Said support frame can comprise two guide elements associated with a support element and which are positioned to the front and rear with respect to the scraper movement direction. The guide elements can flexibly adapt to the geometrical conditions and can be interconnected by a connecting mechanism. If little space is available, the support frame may only comprise a guide element associated with a support element.

In another preferred construction the support frame comprises a spreading mechanism, which brings into and fixes in the desired radial position the components facing the pipe wall. This spreading mechanism can comprise individual spring elements, which are located on several or all the support elements and act radially. Alternatively the spring elements can act tangentially to the circumferential direction of the pipeline, so that through the pipeline curvature a radial component is produced for positioning the support elements.

In a preferred development of the method according to the invention, on expanding the support elements the angle of an axis on which at least two of the components are successively positioned and which is curved in the pipeline circumferential direction, is increased by in each case the same amount with respect to the scraper movement direction.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
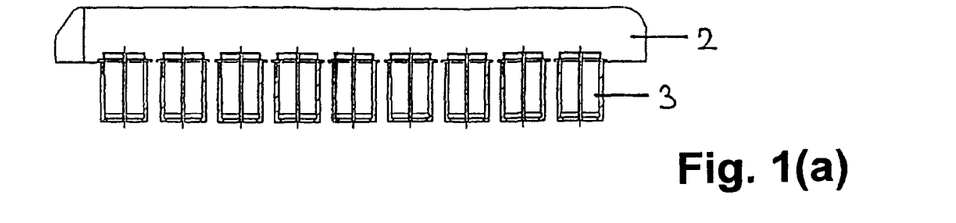
FIG. 1(a) is side view of a support element according to the invention.
Figure 1B:
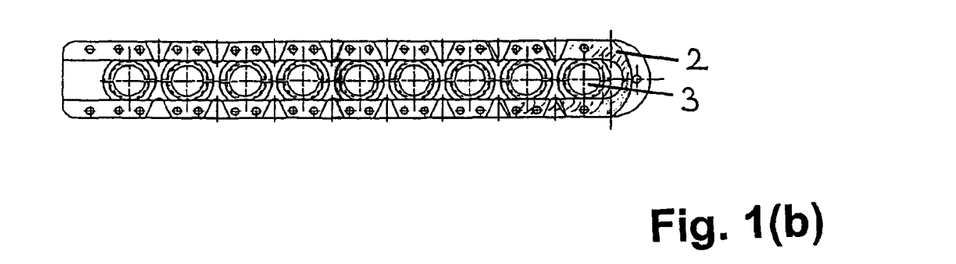
FIG. 1(b) is a plan view of the support element according to the invention.

Referring to the drawings in particular, FIG. 1(a) shows in side view and FIG. 1(b) in plan view a single support element 2 of an inventive support unit usable in a scraper. In the support element extension direction and in the not force-actuated, planar state thereof, the support element has linearly lined up receptors for receiving components 3 facing the pipe wall, such as sensors for performing pipeline tests.

Figure 2A:
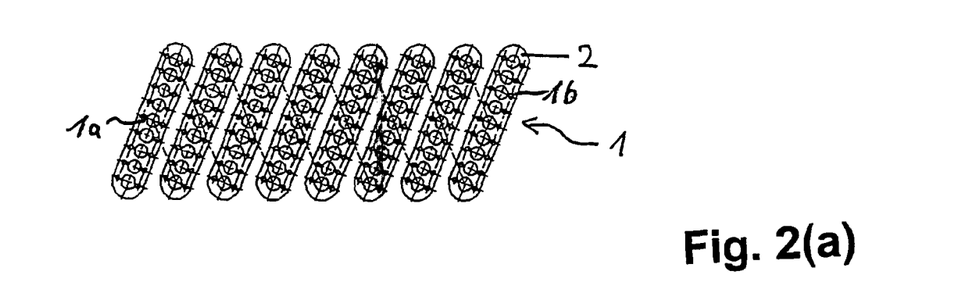
FIG. 2(a) is a diagrammatic plan view of an inventive arrangement of support elements in a first expansion position.

FIG. 2(a) diagrammatically shows in a broadened representation the arrangement of support elements in an inventive support unit 1, in each case two successive support elements 2 being equidistantly spaced, so that also two horizontally adjacent components are equidistantly spaced. In use, the support unit 1 is circularly bent in such a way that its ends 1a, 1b are adjacent (cf. also FIG. 3a, 3b).

Figure 2B:
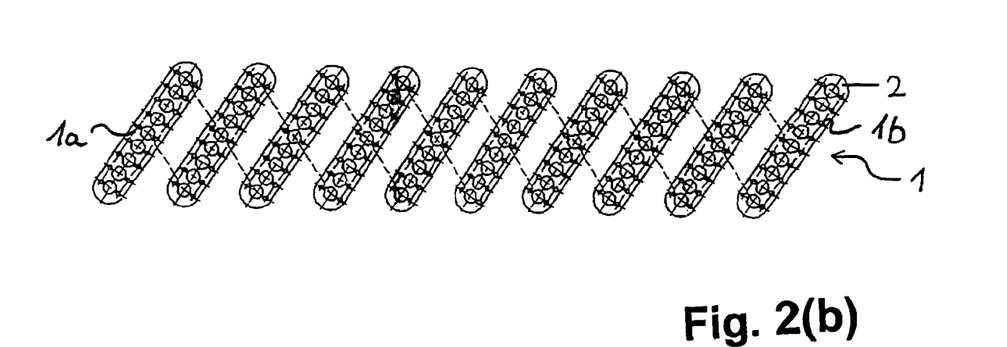
FIG. 2(b) is a diagrammatic plan view of an inventive arrangement of support elements in a second position.

Following an expansion of the closed support unit the spacing between two succeeding support elements 2 is increased to the same amount and as is diagrammatically shown in FIG. 2(b). In order to bring about a uniform, uninterrupted coverage of the traversed surface by components 3, despite an increased spacing during a vertically directed scraper movement, the support elements 2 are uniformly vertically turned compared with FIG. 2(a).

Figure 3A:
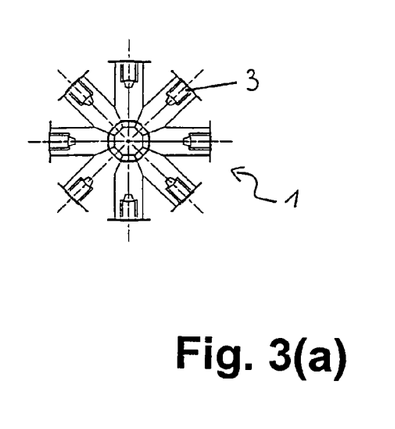
FIG. 3(a) is a diagrammatic cross-section through an inventive arrangement of support elements in a first expansion position.
Figure 3B:
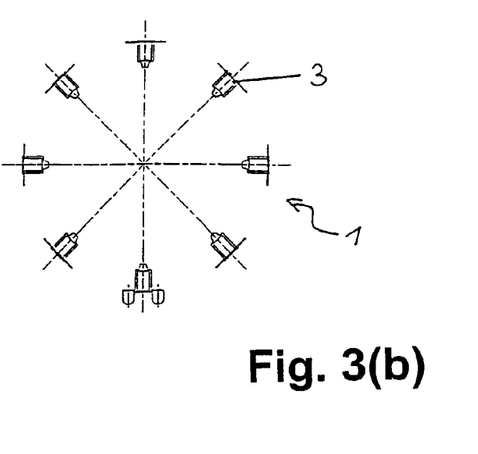
FIG. 3(b) is a diagrammatic cross-section through an inventive arrangement of support elements in a second expansion position.
Figure 4A:
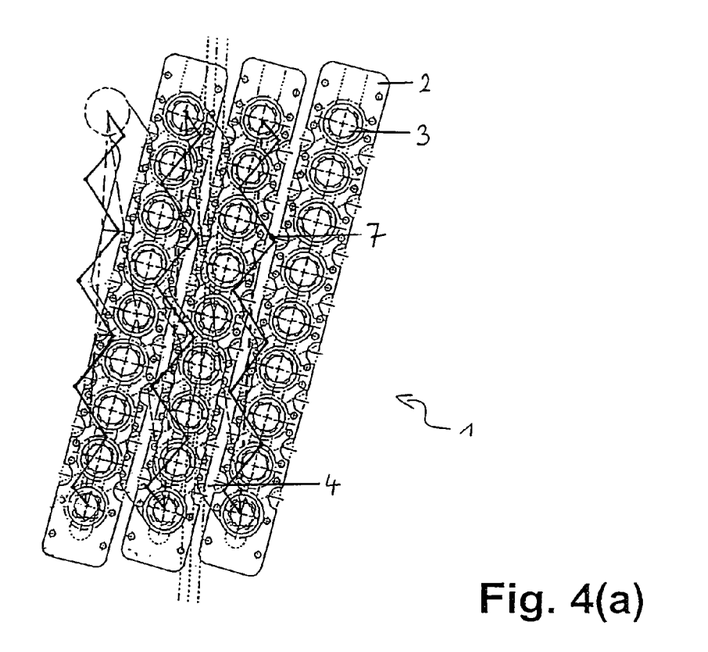
FIG. 4(a) is a plan view of an inventive support unit in a first expansion position.
Figure 4B:
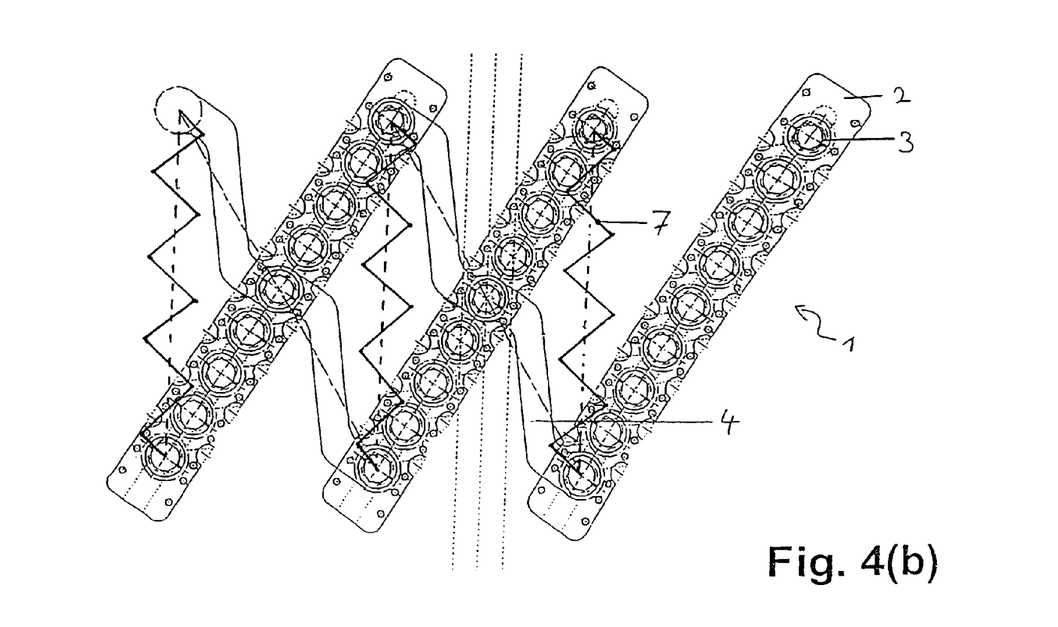
FIG. 4(b) is a plan view of an inventive support unit in a second expansion position.

In a preferred development the support elements 2 are flexibly constructed permitting an adaptation to curved surfaces. Thus, more particularly on traversing pipelines, there is a uniform arrangement of the components 3 in the radial direction on the inner wall. The support elements 3 of FIG. 2 are so arranged on a cylindrical surface that the spacing between the first and last support elements corresponds to the spacing between the remaining support elements. FIG. 3(*a*) is a diagrammatic cross-section through such an arrangement. The components 3 are equidistantly spaced along the pipe circumference. Following an expansion of support unit 1, there is an increase in the spacing between the components, as is apparent from FIG. 3(*b*). The positioning or pivoting of the individual support units takes place on changing the expansion position by means of at least one connecting member articulated to in each case at least two successive support elements. FIG. 4*a*, 4*b* show such a support unit 1 with connecting members 4 having a double S-shape. A connecting member 4 is in each case articulated to three successive support elements 2 in such a way that a pivoting axis is formed in the center of a respective central support element 2 and about which the respective outer support element can be pivoted during an expansion in the scraper movement direction. In addition, two successive support elements 2 are pivotably interconnected by two articulated connecting members in such a way that on pivoting an increase or decrease in the spacing between in each case two successive support elements 2 is brought about to the same extent. To this end the outer joint axes of a respective support element 2 have the same spacing with respect to the central joint axis. In a preferred development two successive support elements are additionally connected at their opposite ends by means of a spring element 7. The resulting spring tension between two successive support elements 2 brings about a pivoting of the connecting members 4 in such a way that a maximum surface is covered by the support unit 1.

Figure 5:
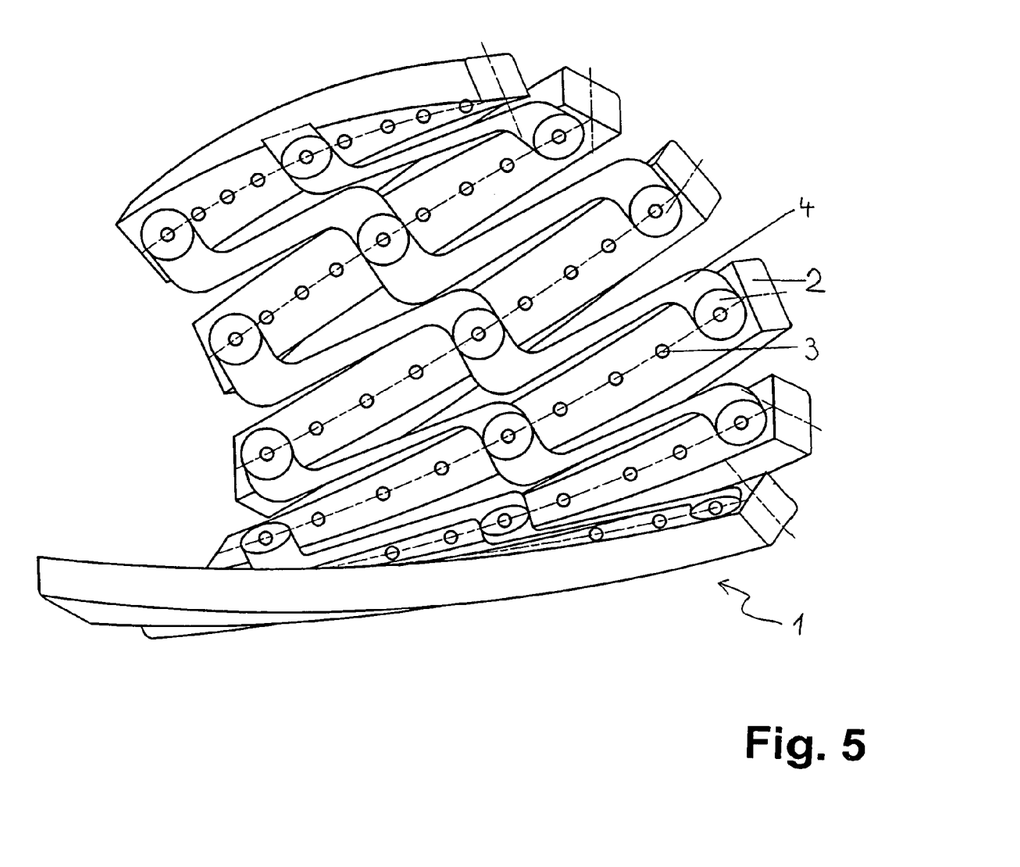
FIG. 5 is a perspective inside view of an inventive support unit, in the case of an adaptation along the inner circumference of a pipeline.
Figure 6:
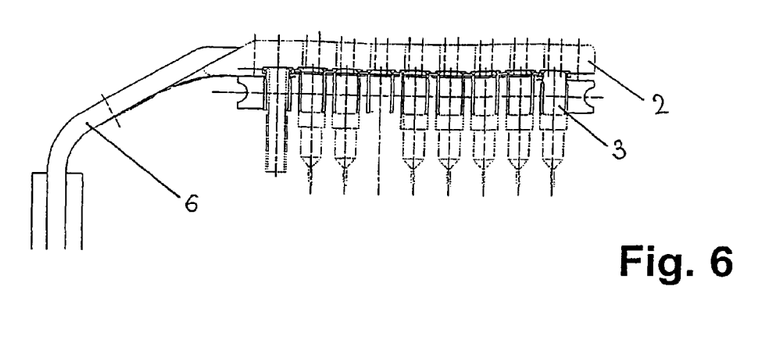
FIG. 6 is a side view through an inventive support element with a support frame guide element.

In a preferred construction the connecting members 4 are flexibly constructed, so that on adapting to the pipeline circumference the support unit 1 has a cylindrical shape or contour, as shown in FIG. 5, and the each of the outer support elements 2 are pivotably interconnected in FIG. 6 by connecting members 4 in the above-described way. The spring elements 7 shown in FIG. 4 bring about a self-guiding adaptation of the support elements 2 along the pipeline inner circumference with random pipe diameters.

Figure 7A:
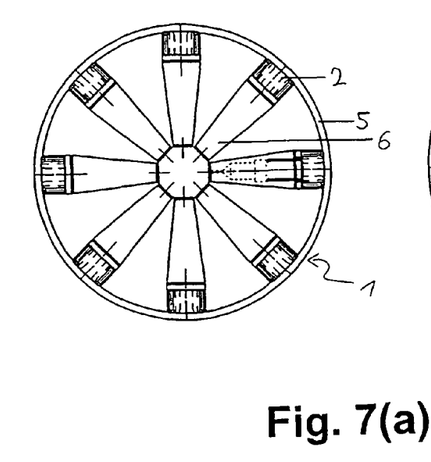
FIG. 7(a) is a diagrammatic cross-section through an inventive arrangement of support elements with a support frame in a first expansion position.
Figure 7B:
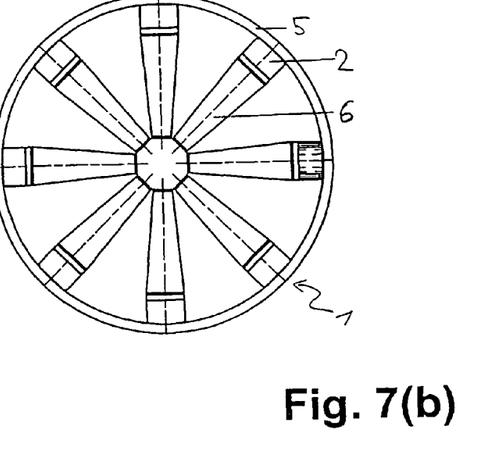
FIG. 7(b) is a diagrammatic cross-section through an inventive arrangement of support elements with a support frame in a second expansion position.
Figure 8A:
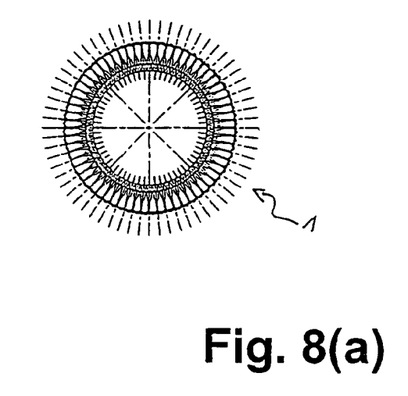
FIG. 8(a) is a diagrammatic front view of an inventive arrangement of support elements in a first expansion position.
Figure 8B:
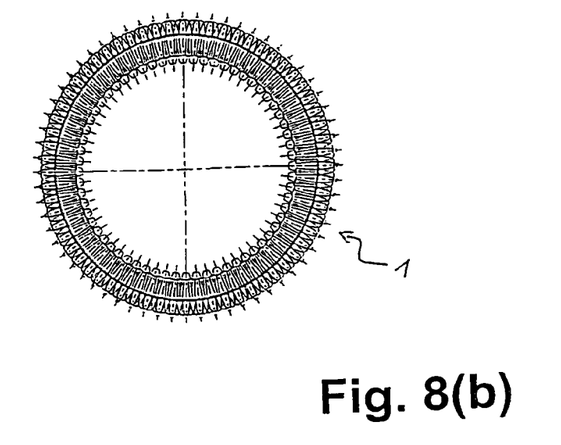
FIG. 8(b) is a diagrammatic front view of an inventive arrangement of support elements in a second expansion position.

For the radial arrangement and fixing of the support elements 2, they are in each case fitted to at least one guide element 6 of a support frame. FIG. 6 shows such a guide element 6 on a support element 2, the flexible construction of the guide element 6 permitting an adaptation to different pipe geometries. FIG. 7 is a diagrammatic cross-section through an inventive arrangement of support elements 2 with in each case a guide element 6 along the inner circumference of the pipe walls, in two different expansion positions. Thus, in the case of a movement through the pipeline there is a uniform, uninterrupted coverage of the surface by components 3 as a result of the increasingly turned support elements 2 with increasing spacing compared with the movement direction and the resulting increased displacement of the components of the support elements in the pipeline circumferential direction. This is illustrated in FIG. 8, which is a diagrammatic front view of support unit 1 in two expansion positions. Both in the less expanded position in FIG. 8(*a*) and in the more expanded position in FIG. 8(*b*), there is an uninterrupted circumferential pipeline coverage.

Figure 9A:
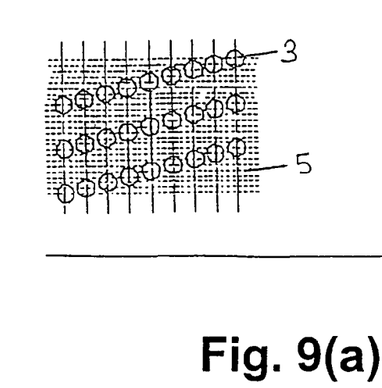
FIG. 9(a) is a diagrammatic side view of an inventive arrangement of components in a first expansion position.
Figure 9B:
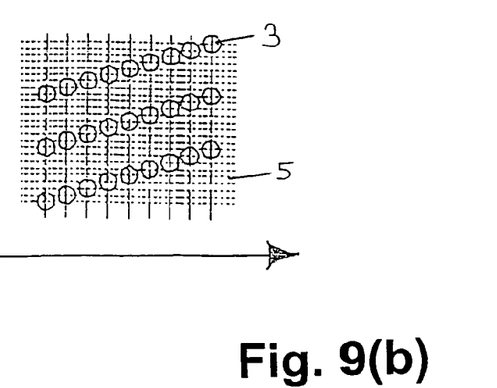
FIG. 9(b) is a diagrammatic side view of an inventive arrangement of components in a second expansion position.

In each expansion position preferably the last component 3 of a support element 2 is connected to the first component of the following support element with the same spacing as between the components of one support element in the circumferential direction of the pipeline 5. This is shown in FIG. 9*a*, 9*b*, in a diagrammatic side view of the support unit 1 in two expansion positions along the pipeline 5. The scraper movement direction is indicated by an arrow. Thus, in the case of different pipeline diameters there is an uninterrupted arrangement of components along the entire pipe circumference and each individual component 3 on the support elements is associated with a specific pipe circumference point. Particularly when carrying out pipeline measurements this leads to the maximum possible measurement resolution for a given number of sensors.

While specific embodiments of the invention have been described in detail to illustrate the application of the principles of the invention, it will be understood that the invention may be embodied otherwise without departing from such principles.

The invention claimed is:

1. A support unit of a scraper movable through a pipeline, the support unit comprising:
   supporting sensors;
   a connecting member;
   radially expandable support elements for said supporting sensors, said supporting sensors facing a pipe wall of the pipeline, said support elements being successively arranged in a circumferential direction of the pipeline, wherein each of said radially expandable support elements is pivotably connected to at least another one of said radially expandable support elements by at least one said connecting member articulated thereto, said radially expandable support elements being pivotable in said circumferential direction such that said radially expandable support elements are equidistantly spaced in each expanded position, said support elements being pivotable about radially extending axes;
   a support frame comprising a spreading mechanism, which brings into and fixes in a desired radial position said supporting sensors facing the pipe wall, said spreading mechanism comprising individual spring elements, which are at least located on several support elements and act radially, said spreading mechanism comprising individual spring elements, which are at least located on several support elements and act tangentially to said circumferential direction of the pipeline and as a result of the action of the pipeline in a coupling direction a radial component is produced for positioning the support elements.

2. A support unit according to claim 1, wherein each of said radially expandable support elements is pivotably connected to said at least another one of said radially expandable support elements by another connecting member.

3. A support unit according to claim 1, wherein said connecting member is located on three successive said radially expandable support elements, said three successive said radially expandable support elements comprising a central support element and two outer support elements, wherein a spacing between outer support elements with respect to said central support element is increased or decreased by a same amount via pivoting said connecting member about an axis on said central support element.

4. A support unit according to claim 1, wherein each said connecting member is located on three successive said radially expandable support elements, said three successive said radially expandable support elements comprising a central support element and two outer support elements, each said connecting member comprising a center piece and end pieces, each said connecting member being arranged with said center piece in a center of said central support element, one of said end pieces of each of said connecting member being arranged on a front end of one of said two outer support elements, another one of said end pieces of each said connecting member being arranged on a rear end of another one of said two outer support elements.

5. A support unit according to claim 1, wherein said at least one connecting member has a double S-shape.

6. A support unit according to claim 1, wherein said radially expandable supporting elements in each expanded position are arranged such that at least two said support sensors are displaced in said circumferential direction of the pipeline.

7. A support unit according to claim 1, wherein said radially expandable support elements in a most compressed expansion position have at least two supporting sensors arranged parallel to a scraper movement direction and said radially expandable support elements in every other expanded position are arranged such that at least two said supporting sensors on each of said radially expandable support elements are displaced in said circumferential direction of the pipeline.

8. A support unit according to claim 1, wherein in each expanded position at least two of said supporting sensors succeed one another on each of said radially expandable support elements in an extension direction of one of said radially expandable support elements and an angle is less than 90° to the scraper movement direction, said one of said support elements being curved in said circumferential direction of the pipeline.

9. A support unit according to claim 1, wherein at least two of said supporting sensors are successively located on each of said radially expandable support elements in an extension direction of one of said radially expandable support elements and an angle thereof with respect to a scraper movement direction increases on expanding said support elements, said one of said radially expandable support elements being curved in said circumferential direction of the pipeline.

10. A support unit according to claim 1, wherein at least two said supporting sensors are successively arranged on each of said radially expandable support elements in an extension direction of one of said radially expandable support elements and an angle thereof with respect to a scraper movement direction decreases upon compressing the support elements, said one of said radially expandable support elements being curved in said circumferential direction of the pipeline.

11. A support unit according to claim 1, wherein said supporting sensors are lined up at the support elements, said supporting sensors performing measurements on the pipeline.

12. A support unit according to claim 1, wherein a number of said radially expandable support elements is adaptable to a diameter or size of the pipe wall.

13. A support unit according to claim 1, wherein a number and spacing of said supporting sensors located on said radially expandable support elements is variable.

14. A support unit according to claim 1, wherein said radially expandable support elements are flexible so as to adapt to a shape of the pipe wall.

15. A support unit according to claim 14, wherein each of said radially expandable support elements is formed by a flexible base element, said flexible base element comprising one of spring steel and plastic.

16. A support unit according to claim 15, wherein said radially expandable support elements are formed from several flexibly interconnected components.

17. A support unit according to claim 1, wherein each said connecting member has the same resistance moment as each of said radially expandable support elements.

18. A support unit according to claim 1, wherein each said connecting member is resiliently constructed, so that the support unit adapts to geometrical conditions determined by the pipe wall.

19. A support unit according to claim 1, wherein said radially expandable support elements are located on said support frame and said radially expandable support elements are supported by said support frame.

20. A support unit according to claim 19, wherein said support frame has two guide elements arranged to a front and rear on said support elements with reference to a scraper movement direction, said support frame flexibly adapting to geometrical conditions and said support frame being interconnected by a connecting mechanism.

21. A support unit according to claim 19, wherein said support frame has a single flexible guide element located at a front on said radially expandable support elements relative to a scraper movement direction.

22. A support unit of a scraper movable through a pipeline, the support unit comprising:
    a plurality of sensors;
    a connecting member;
    a support frame comprising a spreading mechanism, said support frame comprising one or more spring elements;
    a plurality of support elements, one or more of said sensors being arranged on one or more of said support elements, each of said sensors facing in a direction of an interior surface of the pipeline, said support elements being successively arranged in a circumferential direction, wherein each of said support elements is opposite another one of said support elements, each of said support elements being connected to at least another one of said support elements via at least one said connecting member and at least one of said one or more spring elements such that each of said support elements is pivotable about a radially extending axis thereof in said circumferential direction and each of said support elements is movable in a radial direction from an initial position to a radially expanded position, wherein each of said support elements is equidistantly spaced apart from an adjacent support element with each of said support elements in said radially expanded position, said one or more spring elements applying a force in said radial direction and a direction tangential to said circumferential direction.

23. A support unit of a scraper movable through a pipeline, the support unit comprising:
    a plurality of sensors;
    a plurality of connecting members;
    a support frame comprising a spreading mechanism, said spreading mechanism comprising a plurality of spring elements;
    a plurality of support elements, one or more of said sensors being arranged on one or more of said support elements, each of said sensors facing in a direction of an interior surface of the pipeline, each of said connecting members and at least one of said plurality of spring elements connecting two or more said support elements to form a movable arrangement of connected support elements extending in a circumferential direction, wherein each of said support elements is pivotable about a radially extending axis thereof in said circumferential direction and each of said support elements is movable in a radial direction from an initial position to a radially expanded position, each of said support elements being equidistantly spaced apart from an adjacent support element with each of said support elements in said radially expanded position, each of said spring elements applying a force in said radial direction and a direction tangential to said circumferential direction.

* * * * *